United States Patent [19]

Beretta

[11] 4,323,633
[45] Apr. 6, 1982

[54] UV-ABSORBING COMPOUNDS AND PHOTOGRAPHIC ELEMENTS CONTAINING THEM

[75] Inventor: Paolo Beretta, Ferrania, Italy

[73] Assignee: Minnesota Mining and Manufacturing Company, St. Paul, Minn.

[21] Appl. No.: 206,377

[22] Filed: Nov. 13, 1980

[30] Foreign Application Priority Data

Nov. 9, 1979 [IT] Italy .............................. 65207 A/79

[51] Int. Cl.$^3$ .............................................. G03C 1/84
[52] U.S. Cl. ..................................... 430/17; 430/512; 430/517; 430/931; 548/259; 548/269
[58] Field of Search ................... 430/512, 517, 931, 9, 430/17

[56] References Cited

U.S. PATENT DOCUMENTS 3,004,896  10/1961  Heller et al. ......................... 430/931
3,253,921   5/1966  Sawdey ............................... 430/512
3,649,276   3/1972  Sand et al. .......................... 430/512

Primary Examiner—Jack P. Brammer
Attorney, Agent, or Firm—C. Alexander; D. M. Sell; M. A. Litman

[57] ABSTRACT

It is desirable to protect color photographic dye images from ultraviolet radiation which tends to cause dyes to fade.

It has been the practice in the art to add materials into or above the silver halide emulsions which will absorb ultraviolet radiation but allow transmission of visible radiation.

One of the best classes of compounds are the 2-(2'-hydroxyphenyl)-benzotriazoles. These materials absorb ultraviolet radiation well, but tend to have poor solubility, crystallize out of the coating solution and emulsion, and diffuse through the photographic element.

A novel class of substituted 2-(2'-hydroxyphenyl)-benzotriazoles has been found to reduce many of these problems.

14 Claims, No Drawings

ND PHOTOGRAPHIC ELEMENTS CONTAINING THEM

DESCRIPTION

1. Technical Field

The present invention relates to new compounds for use in photography as UV-absorbers and to photographic elements containing them.

2. Background Art

Many compounds are known in the art for use as UV-absorbers. One of the most widely investigated and used classes is the one of the low-molecular weight 2-(2'-hydroxyphenyl)-benzotriazole compounds, as for example described in U.S. Pat. Nos. 3,004,896 and 3,253,921.

It is generally preferred to have high solubility, low tendency for crystallization and non-diffusion characteristics when a compound is to be introduced into a photographic layer coating composition (particularly in the form of a solution in an organic solvent, e.g., a high-boiling water-immiscible organic solvent possibly mixed with a low-boiling organic solvent according to the so-called "dispersion" technique described in U.S. Pat. Nos. 2,322,027; 2,801,170; 2,801,171 and 2,991,177; such dispersion technique briefly consisting of dissolving compounds in a water-immiscible organic solvent and then dispersing the so-prepared solution, as extremely small droplets, in a hydrophilic colloidal binder normally comprising mostly gelatin). It is desired that such compounds not migrate outside the solution both during and after coating and drying.

Particularly, in the absence of appropriate nondiffusion characteristics, the compound would undesirably migrate outside of the layer including it, especially when the photographic material is treated in extreme conditions either of humidity or temperature. A visible adverse effect in these circumstances might be that the compound would break the surface of the emulsion layer and possibly crystallize on it. In the absence of non-diffusion characteristics, the compound could migrate away from where dye images have been formed which are to be protected against fading to the light.

DISCLOSURE OF THE INVENTION

According to the present invention, 2-(2'-hydroxyphenyl)-benzotriazole compounds of low molecular weight have been found with good solubility, low tendency towards crystallization and non-diffusion characteristics. Such compounds are UV-absorbing compounds derived from 2-(2'-hydroxyphenyl)-benzotriazole including two alkyl groups attached to the 2-hydroxyphenyl nucleus and a third alkyl group attached to the benzotriazole nucleus (of course to the phenyl group included therein), characterized in that each of said alkyl groups is a butyl group. Compounds having a useful spectrum of solubility and noncrystallization characteristics with good non-diffusion properties can be obtained by varying the nature of individual butyl groups, which can be of the normal, secondary, tertiary, or iso-type. Some of these compounds are low-melting solid ones, while others are liquid compounds, all of them showing good or improved solubility in the solvents generally used according to the dispersion technique, some of them being completely miscible with such solvents. Representative examples of compounds within the present invention are 2-(2'-hydroxy-3', 5'-ditert.-butyl-phenyl)-5-n-butylbenzotriazole; 2(2'-hydroxy-3'-sec.-butyl-5'-tert.-butyl-phenyl)-5-n-benzotriazole; 2(2'hydroxy-3'-sec.-butyl-5'-tert.-butyl-phenyl)-5-tert.-butylbenzotriazole and 2(2'-hydroxy-3', 5'-ditert.-butylphenyl)-5-tert.-butylbenzotriazole.

DETAILED DESCRIPTION OF THE INVENTION

The present invention refers to UV-absorbing compounds which comprise two alkyl groups attached to the 2'-hydroxyphenyl nucleus and a third alkyl group attached to the benzotriazole nucleus, characterized in that each of said alkyl groups is a butyl group. Preferably, the present invention refers to such compounds having each of said two butyl groups attached to the 3'-and 5' positions and said third butyl group attached to either the 5 or 6 position thereof. Particularly, the present invention most preferably refers to the UV-absorbing compounds 2-(2'-hydroxy-3', 5'-ditert.-butylphenyl)-5-nbutyl-benzotriazole, 2-(2'-hydroxy-3'-sec.-butyl-5'-tert.butyl-phenyl)-5-n-butyl-benzotriazole, 2-(2'-hydroxy-3'-sec.-butyl-5'-tert.-butyl-phenyl)-5-tert.-butylbenzotriazole, and 2-(2'-hydroxy-3', 5'-ditert.-butylbenzotriazole as UV-absorbers.

The present invention refers to a photographic element comprising a supporting base, at least a silver halide photographic emulsion layer and at least an auxiliary layer (which may be an external protective layer, either on the emulsion side or on the base side, or an interlayer), in at least one of said auxiliary or emulsion layers containing at least one (and in some cases mixtures, as known in the art) of the UV-absorbing compounds within the present invention as described above.

The present invention refers to a photographic element as described above, wherein said UV-absorbing compound is included in said auxiliary layer or, even if less usually, to a photographic element which contains said UV-absorbing compound included in said emulsion layer or in both layers.

The present invention preferably refers to a photographic element as described above, wherein said UV-absorbing compound is dissolved in small droplets of a substantially water-immiscible high-boiling organic solvent and the droplets dispersed in the element.

The quantity in which the compounds of the present invention is introduced into the layer preferably ranges from 0.04 to 4, more preferably from 0.1 to 0.8 grams per square meter of the material.

The present invention further refers to a color photographic element containing a colored image made of dyes obtained upon chemical processing, characterized in that said dyes are protected by a UV-absorbing compound of the present invention as described above.

The UV-absorbing compounds of the present invention can be prepared according to known methods. The preferred method includes the reaction of a o-nitro-p-butylphenyl-diazonium salt with a 3,5-dibutyl-phenol to give the respective o-nitrophenylazophenol. This last compound is reduced in an alkaline medium with zinc powder to give the corresponding benzotriazole. The preparation of the UV-absorbing compounds of the present invention is now described in the following examples.

EXAMPLE 1

2-(2'-hydroxy-3', 5'-di-tert.-butylphenyl)5-n-butyl-benzotriazole (compound 1)

2-nitro-4-n-butylaniline intermediate compound 150 g of a 4-n-butyl-aniline were treated with 300 ml of acetic anhydride at 70° C. for 1 hour and then cooled to 10° C. After filtering the solid product on a Buchner funnel and drying at 60° C. under vacuum, 183 g of 4-n-butyl-acetanilide were obtained. 183 g of 4-n-butylacetanilide were dissolved in 300 ml of acetic acid and this solution, cooled at 5°–10° C., was added to a wellstirred mixture obtained by mixing 123 ml of nitric acid at a density of 1.4 and 325 ml of nitric acid at a density of 1.52. The temperature was kept below 5° C. during the whole addition and at the end the stirring was continued for 4 hours. The reaction mixture was then poured into 4 liters of ice and water under stirring, thus obtaining a yellow solid product that was filtered on a Buchner funnel and purified by recrystallization from ethanol. 217.4 g of 2-nitro-4-n-butyl-acetanilide were obtained and treated with 1,500 ml of toluolated ethanol and 600 ml of concentrated hydrochloric acid. The solution obtained was heated to reflux for two hours and the solvents removed under vacuum using a rotary evaporator. The oil residue, the analysis of which is reported hereinbelow, was used for the preparation of compound 1 without further purification.

| | Percent analysis: | |
|---|---|---|
| | Calculated | Found |
| C% | 61.84 | 61.16 |
| H% | 7.27 | 7.28 |
| N% | 14.42 | 14.42 |

2-(2'-hydroxy-3', 5'-di-tert.-butylphenyl)-5-n-butylbenzotriazole (compound 1)

174 g. of 2-nitro-4-n-butyl-aniline were suspended in 1,000 ml of toluolated ethanol and 400 ml of concentrated hydrochloric acid and diazotized at 5°–10° C. with a solution of 63 g of sodium nitrite dissolved in 120 ml of water. The clear diazonium solution was added very slowly to a cold solution obtained by dissolving 186 g of 2,4-di-tert.butyl-phenol in 600 ml of ethanol and 360 ml of sodium hydroxide 30% water solution. The mixture was stirred for two hours at 5° C. and the solid 2-(2'-hydroxy-3', 5'-di-tert.-butyl-phenyl)-3-nitro-4-n-butyl-azo-benzene was filtered out. The raw product was purified by recrystallization from 850 ml of toluolated ethanol, thus obtaining 174 g of pure product, having M.P. at 98°–99° C. This product was dissolved in 1,200 ml of toluolated ethanol and 360 ml of sodium hydroxide 30% water solution and 130 g of zinc powder were slowly added to the wellstirred solution to keep the solution temperature below 30° C. At the end of the addition the reaction mixture was heated to reflux under stirring for two hours, cooled to 30° C. and filtered. The filtered solution was added to 1,000 ml of ice and water and acidified with 500 ml of concentrated hydrochloric acid, thus obtaining a solid product. The solid was filtered on a Buchner funnel, washed with cold water and air dried. The raw product was purified by crystallization from tuluolated ethanol obtaining 132.5 g of pure product having M.P.=101°–101.5° C. Spectral properties $\lambda_{max}=342$ nm.; $\epsilon_{molar}=1.8.10^4$.

| | Percent analysis: | |
|---|---|---|
| | Calculated | Found |
| C% | 75.95 | 75.57 |
| H% | 8.76 | 8.72 |
| N% | 11.07 | 10.98 |

EXAMPLE 2

2-(2'-hydroxy-3'-sec.-butyl-5'-tert.-butyl-phenyl)-5-n-butyl-benzotriazole (compound 2)

110 g of 2-nitro-4-n-butyl-aniline (prepared as described in Example 1) were suspended in 400 ml of toluolated ethanol and 300 ml of concentrated hydrochloric acid and diazotized at 5°–10° C. with 34 g of sodium nitrite dissolved in 100 ml of water, following the same procedure as described for Example 1. The clear diazonium solution was added very slowly to a cold solution obtained by dissolving 74 g of 2-sec.-butyl-4-tert.-butylphenol in 200 ml of ethanol and 150 ml of sodium hydroxide 30% aqueous solution. The mixture obtained was stirred for 2 hours keeping the temperature at 0° C. The solution was then cooled at −10° C. and the gummy solid obtained, 2-(2'-hydroxy-3'-sec.-butyl-5'-tert.-butyl-phenyl)-3-nitro5-n-butyl-azo-benzene, was filtered on a Buchner funnel and washed with cold water. The product was dissolved in 300 ml of ethanol and 20 ml of sodium hydroxide 30% water solution and 130 g of zinc powder were slowly added to the well-stirred solution to keep the temperature below 30° C. At the end of the addition the reaction mixture was heated to reflux under stirring for two hours, cooled to 30° C. and filtered. The filtered solution was poured onto 1,000 ml of ice and water and acidified with 500 ml of concentrated hydrochloric acid, thus obtaining the separation of the product as oil. This oil was extracted with ethyl ether, the ethereal extracts dried over anhydrous sodium sulfate overnight. After filtration and removal of the solvent, the oil was purified by distillation under vacuum, collecting the fraction boiling at 218°–219° C./0.5 mm Hg. The structure has been confirmed by N.M.R. and the acidimetric title (—OH) of the compound resulting in 97% Spectral properties: $\lambda_{max}=342$ nm.; $\epsilon_{molar}=1.8.10^4$.

EXAMPLE 3

2-(2'-3'-sec.-butyl-5'-tert.-butylphenyl)-5-tert.-butyl-benzotriazole (compound 3)

This compound was prepared according to the procedure described in Example 2, using the 2-nitro-4-tert.-butylaniline instead of 2-nitro-4-n-butyl-aniline, thus obtaining a product having a B.P. at 242°–5° C./1 mm Hg and an acidimetric title of 95%.

EXAMPLE 4

2-(2'-hydroxy-3', 5'-ditert.-butylphenyl)-5-tert.-butyl-benzotriazole (compound 4)

This compound was prepared according to the procedure described in Example 1 using 2-nitro-4-tert.-butylaniline instead of 2-nitro-4-n-butyl-aniline, thus obtaining a solid product, having a M.P. of 107°–108° C., a $\lambda_{max}$ of 342 nm. and an $\epsilon_{molar}$ of $1.92.10^4$.

EXAMPLE 5

2-(2'-hydroxy-3', 5'-di-tert.-butylphenyl)-5-sec.-butyl-benzotriazole (compound 5)

2-nitro-4-sec.-butyl-acetanilide intermediate compound 55 g of 4-sec.-butyl-aniline were treated with 150 ml of acetic anhydride at 60° C. for half an hour and then cooled at 10° C.; the reaction mixture was poured into one liter of water and ice under stirring. The solid product was filtered on a Buchner funnel, washed with water up to neutrality and dried at 60° C. under vacuum. The 65 g of 4-sec.-butyl-acetanilide, thus obtained, were added to 180 ml of nitric acid at a density of 1.44 cooled at −10° C. During the whole addition, the temperature was kept between −10° and −8° C. and at the end of the addition the stirring was continued for 2 hours. The reaction mixture was then poured into water and ice under stirring, thus obtaining a fluid pitch. The pitch was suspended in chloroform thus obtaining a solution and a solid residue which was removed. The chloroform solution was dried on anhydrous sodium sulfate overnight, filtered and evaporated under vacuum, thus obtaining 60 g of a yellow oil which was used at it was eithout any further purification.

2-(2'-hydroxy-3', 5'-tert.-butylphenyl)-5-sec.-butyl-benzotriazole (compound 5)

60 g of 2-nitro-4-sec.-butyl-acetanilide was treated with 200 ml of toluolated ethanol and 120 ml of concentrated hydrochloric acid. The obtained solution was heated to reflux for 2 hours, cooled at −10° C. and diazotized with a solution obtained by dissolving 17.5 g of sodium nitrite in 50 ml of water. The solution, clarified upon filtration of the diazonium salt, was very slowly added to a cold (8° ÷ −10° C.) solution obtained by dissolving 50 g of 2,4-di-tert.-butylphenol in 200 ml of ethanol and 100 ml of a 30% water solution of sodium hydroxide. At the end of the addition, the mixture was stirred for 4 hours and the wax solid thus obtained was separated upon decantation and purified upon recrystallization from methanol, thus obtaining 24 g of 2-(2'-hydroxy-3', 5+-di-tert.-butylphenyl)-3-nitro-4-sec.-butyl-azo-benzene with a M.P. equal to 111° C., after filtration on a Buchner funnel and drying under vacuum at 60° C. 24 g of such product were dissolved in 200 ml of toluolated ethanol and 80 ml of a 30% water solution of sodium hydroxide and treated to reflux with 22 g of zinc powder, added very slowly in small portions. At the end of the addition the reaction mixture was heated to reflux for one hour, cooled, filtered and poured into 800 ml of water and ice acidified with 100 ml of concentrated hydrochloric acid. The pitchy solid, thus obtained, was separated upon decantation and crystallized from toluolated ethanol, thus obtaining 12 g of pure product with a M.P. equal to 77°–78° C. Spectral characteristics: $\lambda_{max} = 340$ mn.; $\epsilon_{molar} = 1.9 \cdot 10^4$.

|    | Percent analysis: | |
|----|------------|--------|
|    | Calculated | Found  |
| C% | 75.95      | 75.99  |
| H% | 8.76       | 8.85   |
| N% | 11.07      | 10.97  |

The invention is now illustrated in the following examples, having the below listed compounds well known in the art as a reference:

Compound A: 2-(2'-hydroxy-3', 5'-ditert.-butylphenyl)-benzotriazole

Compound B: 2-(2'-hydroxy-3', 5'-ditert.-amylphenyl-benzotriazole

EXAMPLE 6

0.4 g of the UV-absorbing compounds were dissolved in ethyl acetate using a glass tube having 0.5 cm inner diameter and heated to 77° C. The material was then cooled to room temperature for 30 minutes and then cooled by immersion in icewater and allowed to stand at 5° C. in a refrigerator. The separation of crystals during these operations was thus observed.

(a) Using 1.2 ml of boiline ethyl acetate a saturated solution was obtained for Compound A. Crystals began to separate immediately at 60° C. and the content solidified completely after 2 minutes.

(b) Using 0.5 ml of boiline ethyl acetate a saturated solution was obtained for Compound B. No crystal was observed when the solution was cooled at room temperature, but when the temperature was down to 5° C., the content solidified completely after 1 minute.

(c) Using 0.8 ml of boiling ethyl acetate a saturated solution was obtained for Compound 1 of the present invention. No crystal was observed when the solution was cooled at room temperature, but when the temperature was down to 5° C., the content solidified completely after three minutes.

(d) Using Compound 2 of the present invention a complete solubility of the oil in ethyl acetate at room temperature was obtained. No separation of the two phases was observed after 12 hours.

EXAMPLE 7

Several dispersions of UV-absorbing compounds were prepared according to the following formula:

| UV-absorbing compound | 6 g |
|---|---|
| dibutylphthalate | 0.9 ml |
| tricresylphosphate | 0.9 ml |
| ethyl acetate | 10 ml |
| gelatin | 2.4 g |
| Hostapur 10% (alkylsulfonate surfactant) | 2.5 ml |
| water to make | 100 ml |

After 8 days at room temperature (20° C.), the dispersions were mixed with gelatin and a suitable surfactant and coated on a triacetate base at a ratio of 51.6 g of the product per 100 g of gelatin, so as to obtain a layer with a thickness of 1.2μ. The coatings were examined under a polarized light microscope to find the presence of crystals; the examination was performed on 10 samples per coating; the results are reported in the following table.

| Coating | UV-absorbing compound | Presence of crystals |
|---|---|---|
| 1 | Compound B | ≅25 per crystals per field on all samples |
| 2 | Compound 1 | Very rare crystals on two samples |
| 3 | Compound 2 | No crystal |

EXAMPLE 8

An emulsion layer for color paper, chromatically sensitized to the green and containing a magenta coupler, was coated with the gelatin layers containing the UV-absorbing compounds made according to the formula of Example 6 so as to obtain 0.57 g of UV-absorber per square meter. The coating was further completed with a gelatin protective layer, both gelatin layers containing the usual surfactants and known hardeners. Film strips, thus obtained, were exposed through a graduated wedge to the green light and then developed in a 3M CPP2 processing line for color paper. The developed strips were read at the densitometer. The sensitopetric characteristics are reported in the following table:

| Film | UV-Absorber | $D_{min}$ | Sensitivity | Average contrast |
| --- | --- | --- | --- | --- |
| 1 | Compound B | 0.11 | 2.62 | 2.32 |
| 2 | Compound 1 | 0.11 | 2.69 | 2.54 |
| 3 | Compound 2 | 0.10 | 2.69 | 2.72 |

The compounds of the present invention thus are shown to have less adverse effect upon the sensitometry of the emulsion than Compound B of the prior art.

EXAMPLE 9

A triacetate supporting base was coated with the following layers in the indicated order: two red-sensitive silver halide emulsion layers containing a cyan coupler, an intermediate layer, two green-sensitive silver halide emulsion layers containing a magenta coupler, a yellow filtering layer, a blue-sensitive silver halide emulsion layer containing a yellow coupler; the outmost blue-sensitive layer had been coated with a gelatin protective layer containing 0.29 g/m² of the UV-absorbing compound, such a layer having been obtained from a coating composition formed from a gelatin and surfactant water solution containing a dispersion of the following formula:

| | |
| --- | --- |
| UV-absorbing compound | 8 g |
| diethyllauramide | 4.1 g |
| tricresylphosphate | 1.35 g |
| ethylacetate | 15 g |
| gelatin 8% | 30 g |
| Cosmopon ® (surfactant) 5% | 5 g |
| water to make | 100 ml |

Strips of the film, thus obtained, were incubated for 48 hours at 20° C. and 95% relative humidity and then observed at their surfaces with a 10 magnification lens; in the case of a film having in the external protective layer thereof reference compound B as UV-absorber, the presence of several crystals was observed, while in the case of a film having in the external protective layer thereof Compound 2 of the present invention as UV-absorber, the presence of no crystals were observed.

The present invention is not limited to photographic elements with a particular type of emulsion or of silver halide; it can therefore find an application with photograhic elements containing different types of emulsion or of silver halides, as for instance those described in Research Disclosure 17643, Item I, December 1978.

The employable emulsions can be chemically and optically sensitized as described in Research Disclosure 17643, Items III and IV, December 1978; they can contain optical brighteners, antifogging agents and stabilizers, filtering and antihalo dyes, hardeners, coating aids, plasticizers and lubricants and other auxiliary substances, as described for instance in Research Disclosure 17643, Items, V, VI, VIII, X, XI and XII, December 1978.

The layers of the photographic emulsion and the layers of the photographic element can contain various colloids, alone or in combination, as binding materials, as described for instance in Research Disclosure 17643, Item IX, December 1978.

The employable photographic elements can contain orthochromatic or panchromatic emulsions, as well as unsensitized emulsions. In particular and more preferably, they can be emulsions for color photography containing color forming couplers, as described in Research Disclosure 17643, Item VII, December 1978.

The above described emulsions can be coated on a variety of supporting bases and with a variety of coating methods, as described in Research Disclosure 17643, Items XV and XVII, December 1978.

Finally, the light-sensitive silver halides contained in the photographic elements after exposure can be processed to form a visible image according to processing formulas and techniques, as described in Research Disclosure 17643, Item XIX, December 1978.

I claim:

1. A photographic element comprising a support, at least one silver halide photographic emulsion layer and at least one auxiliary layer, said photographic element being characterized by having in at least one of said silver halide emulsion layer and said auxiliary layer an ultraviolet radiation absorbing 2-(2'-hydroxyphenyl)-benzotriazole compound having two butyl groups attached to the 2'-hydroxyphenyl nucleus and a third butyl group attached to the benzotriazole nucleus.

2. A photographic element according to claim 1, in which the compound is included in said auxiliary layer.

3. A photographic element according to claim 1, in which the compound is included in said emulsion layer.

4. The photograhic element of claim 1 wherein said two butyl groups are attached to the 3' and 5' positions of the 2'-hydroxyphenyl nucleus and said third butyl group is attached to either the 5 or 6 position of the benzotriazole nucleus.

5. The photographic element of claim 4 wherein said ultraviolet radiation absorbing compound is 2-(2'-hydroxy-3',5'-ditert.-butylphenyl)-5-n-butyl-benzotriazole.

6. The photographic element of claim 4 wherein said ultraviolet radiation absorbing compound is 2-(2'-hydroxy-3'-sec.-butyl-5'-tert.-butylphenyl)-5-n-butyl-benzotriazole.

7. The photographic element of claim 4 wherein said ultraviolet radiation absorbing compound is 2-(2'-hydroxy-3'-sec.-butyl-5'-tert.-butyl-phenyl)-5-tert.-butyl-benzotriazole.

8. The photographic element of claim 4 wherein said ultraviolet radiation absorbing compound is 2-(2'-hydroxy-3'-5'-ditert.-butylphenyl)-5-tert.-butyl-benzotriazole.

9. The photographic element of claims 1, 5, 6, 7, or 8 wherein said ultraviolet radiation absorbing compound is included within said at least one silver halide photographic emulsion layer and/or said auxiliary layer dissolved in small droplets of high-temperature boiling, substantially water immiscible, organic solvent dispersed therein.

10. An imaged and developed photographic element including a dye image characterized by having in the same layer as the dye image or in an auxiliary layer an ultraviolet radiation absorbing 2-(2'-hydroxyphenyl)-benzotriazole compound having two butyl groups attached to the 2'-hydroxyphenyl nucleus and a third butyl group attached to the benzotriazole nucleus.

11. The element of claim 10 wherein said ultraviolet radiation absorbing compound has said two butyl groups attached to the 3' and 5' positions of said 2'-hydroxyphenyl nucleus and said third butyl group attached to either the 5 or 6 position of said benzotriazole nucleus.

12. The photographic element of claims 1 and 4 wherein said ultraviolet radiation absorbing compound is present in at least one of said silver halide emulsion layer and said auxiliary layer in an amount of from 0.04 to 4 grams per square meter.

13. The photographic element of claim 9 wherein said ultraviolet radiation absorbing compound is present in at least one of said silver halide emulsion layer and said auxiliary layer in an amount of from 0.04 to 4 grams per square meter.

14. The element of claims 10 and 11 wherein said ultraviolet radiation absorbing compound is present in at least one of said dye image layer and said auxiliary layer in an amount from 0.04 to 4 grams per square meter.

* * * * *

UNITED STATES PATENT AND TRADEMARK OFFICE
CERTIFICATE OF CORRECTION

PATENT NO. : 4,323,633
DATED : April 6, 1982
INVENTOR(S) : Paolo Beretta

It is certified that error appears in the above—identified patent and that said Letters Patent is hereby corrected as shown below:

Column 4, line 47, delete "resulting" and insert --resulted-- in its place.

Column 4, line 51, delete "2-(2'-3'-sec.-butyl-. . ." and insert --2-(2'-hydroxy-3'-sec.-butyl-. . .-- in its place.

Column 6, lines 18 and 22, delete "boiline" and insert --boiling-- in its place in both instances.

Signed and Sealed this

Twelfth Day of October 1982

[SEAL]

Attest:

GERALD J. MOSSINGHOFF

Attesting Officer    Commissioner of Patents and Trademarks